(12) United States Patent
Yoshida et al.

(10) Patent No.: US 6,827,949 B2
(45) Date of Patent: Dec. 7, 2004

(54) WOOD PRESERVATIVE

(75) Inventors: Shinji Yoshida, Osaka (JP); Munekazu Iinuma, Gifu (JP)

(73) Assignee: Takeda Chemical Industries, Ltd., Osaka (JP)

( * ) Notice: Subject to any disclaimer, the term of this patent is extended or adjusted under 35 U.S.C. 154(b) by 329 days.

(21) Appl. No.: 10/119,710

(22) Filed: Apr. 11, 2002

(65) Prior Publication Data

US 2003/0060504 A1 Mar. 27, 2003

(30) Foreign Application Priority Data

Apr. 11, 2001 (JP) .................................... 2001-112546
Dec. 27, 2001 (JP) .................................... 2001-396441

(51) Int. Cl.$^7$ .............................................. A61K 35/78
(52) U.S. Cl. ................................................ 424/725
(58) Field of Search ........................................ 424/725

(56) References Cited

FOREIGN PATENT DOCUMENTS

| JP | 8-133941 | 5/1996 |
|---|---|---|
| JP | 9-328493 | 12/1997 |
| JP | 2001-316260 | 11/2001 |

OTHER PUBLICATIONS

S. Tawata et al., "Syntheses and Biological Activities of Dihydro–5,6–dehydrokawain Derivatives", Biosci. Biotech. Biochem., vol. 60, No. 10, pp. 1643–1645, 1996.
C.P. Locher et al., "Anti–microbial activity and anti–complement activity of extracts obtained from selected Hawaiian medicinal plants", Journal of Ethnopharmacology, vol. 49, pp. 23–32, 1995.
Executive Summary Kava Kava, No. 1998, 12 pages.
G. Boonen et al., "Influence of Genuine Kavapyrone Enantiomers on the GABA, Binding Site", Planta Medica, vol. 64, 1998, pp. 504–506.

F. Keller et al., "LLOYDIA", vol. 26, No. 1, Mar. 1963, pp. 1–15.

T. Reffstrup et al., "The preparation of 4–Hydroxy–5, 6–dihydro–2–pyrones and Their Conversion to Kawa–lactones as well as to Other Precursors of Naturally Occuring 2–Pyrones", Acta Chemical Scandinavica B30, 1976, pp. 613–618.

*Primary Examiner*—Michael Meller
(74) *Attorney, Agent, or Firm*—Wenderoth, Lind & Ponack, L.L.P.

(57) ABSTRACT

A wood preservative that comprises as an active ingredient a Piper methysticum, plant or a processed product thereof or a compound represented by Formula (I):

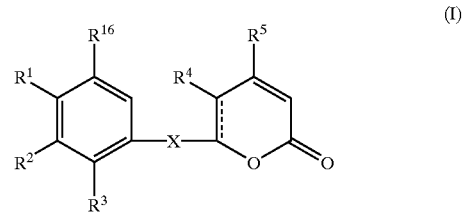

wherein $R^1$, $R^2$, $R^3$, $R^4$ and $R^{16}$ are same or different and each denotes a hydrogen atom, hydroxy or a $C_{1-4}$ alkoxy, or $R^1$ and $R^2$ are taken together to form a group represented by —O—$(CH_2)_n$—O— wherein n is an integer of 1 to 3, $R^5$ is a $C_{1-4}$ alkoxy and X is —CH=CH—, —$CH_2$—$CH_2$— or epoxyethylene, and the bond:

≡ denotes a single bond or a double bond can prevent the attacking wood by an insect harmful to the wood and also prevents the appearance and the growth of a wood-rotting fungus or a wood- staining fungus while being highly safe to humans and animals without exerting no adverse effect on the environment.

10 Claims, 1 Drawing Sheet

WOOD PRESERVATIVE

FIELD OF THE INVENTION

The present invention relates to a wood preservative, particularly a wood attacking-, decaying- and staining-inhibitory composition. More particularly, to a wood attacking-, decaying- and staining-inhibitory composition against a wood damage by an insect which is harmful to wood such as termites and *Lyctus brunneus* Stephens which damage a building or a furniture made of wood and also by a wood decaying microorganism including a brown-rot fungus such as *Fomitopsis palustris* and a white-rot fungus such as *Trametes versicolor* and also against a dirt by a wood-staining fungus such as *Aspergillus niger* and *Aureobasidium pullulans*, as well as a method and use for producing the same.

BACKGROUND OF THE INVENTION

Various known wood preservatives are employed in order to control insects harmful to wood, such as termites and *Lyctus brunneus* Stephens and also to prevent decaying by a wood-rot fungus such as *Fomitopsis palustris* and *Coniophora puteana* or a staining by a wood-staining fungus such as *Aspergillus niger* and *Aureobasidium pullulans*. However, any of such known wood preservatives badly affects the safety in humans and animals as well as the environment, and may destroy the ecosystem of nature.

An objective of the present invention is to provide a wood preservative which exhibits an excellent insect-controlling activity against a harmful insect as well as a high anti-decaying activity against a wood-rot fungus and a high antifungal activity against a fungal growing in wood and staining the wood.

Another objective of the invention is to provide a wood preservative that is highly safe to humans and animals and does not affect the environment adversely.

Still another objective of the invention is to provide a wood preservative capable of controlling an insect harmful to a wood, a wood-rot fungus and a wood-staining fungus reliably and efficiently.

SUMMARY OF THE INVENTION

In order to accomplish the objectives described above, the inventors have conducted extensive study to examine various material and compounds and have found that a *Piper methysticum* plant or a processed product thereof, or a chemical compound obtainable from the plant or derivatives thereof exhibit an excellent effect for preserving wood without any bad influence on mammals and environment.

Thus, the present invention is:

1. A wood preservative comprising as an active ingredient a *Piper methysticum* plant or a processed product thereof, or a compound represented by Formula (I):

wherein $R^1$, $R^2$, $R^3$, $R^4$ and $R^{16}$ are same or different and each denotes a hydrogen atom, hydroxy or a $C_{1-4}$ alkoxy, or $R^1$ and $R^2$ are taken together to form a group represented by —O—$(CH_2)_n$—O— wherein n is an integer of 1 to 3, $R^5$ is a $C_{1-4}$ alkoxy and X is —CH=CH—, —$CH_2$—$CH_2$— or epoxyethylene, and the bond:

===== denotes a single bond or a double bond.

2. The wood preservative according to 1. which is an insect-controlling agent.
3. The wood preservative according to 1. which is an anti-decaying agent.
4. The wood preservative according to 1. which is an anti-fungal agent.
5. The wood preservative according to 1. which is a termite-controlling agent.
6. The wood preservative according to 1. wherein said *Piper methysticum* plant or processed product thereof is a stem, leaf or root of a *Piper methysticum* plant or a processed product thereof.
7. The wood preservative according to 6. wherein the processed product is a dry powder or an extract of a stem, leaf or root of *Piper methysticum*.
8. The wood preservative according to 1. wherein the compound represented by the formula (I) is a compound represented by Formula (II):

wherein $R^6$ is hydroxy or a $C_{1-4}$ alkoxy, $R^7$ is a hydrogen atom, hydroxy or a $C_{1-4}$ alkoxy, or $R^6$ and $R^7$ are taken together to form a group represented by —O—$(CH_2)_n$—O— wherein n is 1 or 2, $R^8$ is a hydrogen atom or a $C_{1-4}$ alkoxy, $R^9$ is hydroxy or a $C_{1-4}$ alkoxy, $R^{17}$ is a hydrogen atom, hydroxy or a $C_{1-4}$ alkoxy and X is defined as described above, or a compound represented by Formula (III):

wherein $R^{10}$ is a hydrogen atom, hydroxy or a $C_{1-4}$ alkoxy, $R^{11}$ is a hydrogen atom or hydroxy, or $R^{10}$ and $R^{11}$ are taken together to form a group represented by —O—

$(CH_2)_n$—O— wherein n is 1 or 2, $R^{12}$ is a hydrogen atom or hydroxy, $R^{13}$ is a $C_{1-4}$ alkoxy, $R^{18}$ is a hydrogen atom, hydroxy or a $C_{1-4}$ alkoxy and X is defined as described above.

9. The wood preservative according to 1. wherein a compound represented by Formula (I) is:
   (1) kawain, or kavain
   (2) 7,8-dihydrokawain, or 7,8-dihydrokavain
   (3) yangonin,
   (4) 5,6,7,8-tetrahydroyangonin,
   (5) methysticin,
   (6) 7,8-dihydromethysticin,
   (7) cis-5-hydroxykawain, or cis-5-hydroxykavain
   (8) 11-methoxy-12-hydroxy-5,6-dehydrokawain, or 11-methoxy-12-hydroxy-5,6-dehydrokavain
   (9) 7,8-dihydroyangonin,
   (10) 5,6-dihydroyangonin,
   (11) 11-methoxyyangonin,
   (12) 10-methoxyyangonin,
   (13) 11-hydroxyyangonin or,
   (14) 5,6-dehydromethysticin.

10. The wood preservative according to 1. wherein the compound represented by the formula (I) is a compound represented by Formula (IV):

(IV)

wherein each of $R^{14}$ and $R^{15}$ is a hydrogen atom or they are taken together to form methylenedioxy, and X is defined as described above.

11. A method for preserving wood which comprises treating wood with an effective amount of a *Piper methysticum* plant or processed product thereof, or a compound represented by Formula (I).

(I)

wherein $R^1$, $R^2$, $R^3$, $R^4$ and $R^{16}$ are same or different and each denotes a hydrogen atom, hydroxy or a $C_{1-4}$ alkoxy, or $R^1$ and $R^2$ are taken together to form a group represented by —O—$(CH_2)_n$—O— wherein n is an integer of 1 to 3, $R^5$ is a $C_{1-4}$ alkoxy and X is —CH=CH—, —$CH_2$—$CH_2$— or epoxyethylene, and the bond:

===== denotes a single bond or a double bond.

12. Use of a *Piper methysticum* plant or processed product thereof, or the compound represented by the formula (I) for a production of the wood preservative.

Explanation of Signals
1. A pine bait
2. Pulverized stems or leaves of *Piper methysticum*
3. Soil
4. A gateway for moving of a termite
5. A termite

DETAILED DESCRIPTION OF THE INVENTION

The present invention is a wood preservative, more particularly, a wood attacking-, decaying- and staining-inhibitory composition containing as an active ingredient *Piper methysticum* plant or processed product thereof or a compound represented by Formula (I).

The term wood preservative means protecting wood from the attacking, decaying and staining. The term wood-attacking referred to here means a damage on wood by an insect harmful to the wood such as termites and *Lyctus brunneus* Stephens, the term wood decaying means a decaying of wood caused by a rot fungus such as *Fomitopsis palustris* and *Coniophora puteana*, and the term wood staining means staining wood for example by *Aspergillus niger* and *Aureobasidium pullulans*.

By applying the wood preservative of the invention to wood or by immersing wood in the composition, the wood attacking, decaying or staining mentioned above can safely be prevented without destroying the ecosystem of nature.

In the present invention, *Piper methysticum* plant, processed product thereof, and the compounds represented by Formula (I) shown above can be employed solely or in combination.

A plant of *Piper methysticum* and *Piper wichmannii*, which is an original plant of the *Piper methysticum* occur over the region from New Guinea to Polynesia. A susterranean stem of the plants has been utilized by local people as their folk medicine and served on important and ceremonial occasions, like coffee or tea, but its terrestrial stem is discarded without being utilized.

The plant *Piper methysticum* is an evergreen herb and 1.5–3.0 m high, belongs to genus Piper, family Piperaceae. The leaf is heart shaped, 10–20 cm long and comes out alternately from a stem. The plant of *Piper methysticum* is referred as "kawa", "kava", "kava-kava" or "yangona" etc. according to the area.

In the present invention, a processed product of the plant is, for example, an extract or an exudate. A processed product means a product obtained by treating the stem, leaf, root and/or fruit of the plants for example b means of drying and cutting, extraction, exudate recovery, grinding and the like. A further extraction may be performed to obtain an active ingredient of the invention. Moreover, when a plant is extracted, the use is made of not only the extract but also of the extraction residue as an effective material for the wood preservative of the present invention.

In the invention, the term "exudate" means not only an exudate obtained from the stem, leaf, root and/or fruit of the plant, but also any exudate oozed out of the plant.

An extract described can be obtained by any conventional methods. For example, a plant listed above may be cut, dried and ground if necessary and then extracted with a suitable extraction solvent under atmospheric pressure or under pressure in an autoclave or a pressurizing reactor at room temperature or with heating, and then filtered if necessary and then concentrated to obtain the extract.

An extraction solvent may for example be water; an alcohol including a monohydric alcohol such as methanol, ethanol, n-propanol, i-propanol, n-butanol, i-butanol, sec-butanol, t-butanol, n-octanol, 2-butyl octanol, tridecanol, iso-tridecanol, 2-hexyl 1-octanol, 2-butyl-1-decanol, 2-hexyl-1-decanol, lauryl alcohol and cyclohexanol as well as a dihydric or polyhydric alcohol such as ethylene glycol, propylene glycol and glycerin; an ether such as ethyl ether, propyl ether, isopropyl ether, dimethoxyethane, a cyclic ether, for example, dioxane and tetrahydrofuran, a mono- or dialkylene glycol monoalkyl ether, for example, ethylene glycol monomethyl ether; a ketone such as acetone, methyl ethyl ketone, methyl isobutyl ketone and cyclohexanone; an ester such as ethyl acetate, butyl acetate and n-butyl laurate; a halogenated hydrocarbon such as carbon tetrachloride, chloroform, dichloromethane and 1,2-dichloroethane; an aliphatic hydrocarbon such as hexane and octane; an alicyclic hydrocarbon such as cyclohexane and cycloheptane; an aromatic hydrocarbon such as benzene, toluene and xylene; a nitrile such as acetonitrile; a carboxylic acid such as formic acid, acetic acid ,oleic acid, octanoic acid, nonanoic acid, decanoic acid and iso-decanoic acid; an aprotic polar solvent such as N,N-dimethylformamide, dimethylsulfoxide, pyridine and the like. Any of these solvents may be employed alone or in combination with each other.

The stem, leaf, root and fruit of a *Piper methysticum* plant may preferably be extracted for example with preferably, monohydric alcohols, dihydric alcohols and ketones, specifically, methanol, propylene glycol and acetone.

The amount of an extraction solvent listed above may vary as long as it does not affect the extraction efficiency and operation adversely, and may for example be 50 to 10000 parts by weight, preferably 100 to 2000 parts by weight based on 100 parts by weight of the material to be extracted. The extraction temperature may for example be 0 to 150° C., preferably 10 to 120° C.

The most compounds represented by the formula (I) are contained in the *Piper methysticum* plant or a processed product thereof. Therefore some of the compounds can be obtained from the plant or the processed products thereof by extraction and separation, for example. Some of the compounds can also be prepared by chemical synthesis.

In Formulae (I) to (III) shown above, a $C_{1-4}$ alkoxy represented by each of $R^1$ to $R^{18}$ may for example be methoxy, ethoxy, n-propoxy, i-propoxy, n-butoxy and i-butoxy. A group represented by —O—$(CH_2)_n$—O— wherein n is an integer of 1 to 3 which is formed when $R^1$ and $R^2$, $R^6$ and $R^7$ or $R^{11}$ and $R^{12}$ are taken together may for example be —O—$CH_2$—O— and —O—$(CH_2)_2$—O—.

In Formula (I), the epoxyethylene represented by X is a group represented by Formula:

The compound represented by Formula (III) wherein all of $R^{10}$, $R^{11}$ and $R^{12}$ are hydrogen atoms, X is —CH=CH— and $R^{13}$ is $OCH_3$ is the compound called "kawain" or "kavain" as a general name.

The compound represented by Formula (II) wherein $R^6$ is $OCH_3$, each of $R^7$ and $R^8$ is a hydrogen atom H, $R^9$ is $OCH_3$ and X is —CH=CH— is the compound called "yangonin" as a general name.

The compound represented by Formula (III) wherein $R^{10}$ and $R^{11}$ taken together form —O—$CH_2$—O—, $R^{12}$ is a hydrogen atom, $R^{13}$ is $OCH_3$ and X is —CH=CH— is the compound called "methysticin" as a general name.

A compound represented by Formula (I) has an activity of preventing the ingestion of a wood by an insect harmful to the wood and preventing the appearance and the growth of a wood-rot fungus or a wood-staining fungus while being highly safe to humans and animals without exerting no adverse effect on the environment.

Among the compounds represented by Formula (I), the compounds represented by Formulae (II), (III) and (IV) have excellent effects and the compound represented by Formula (IV) is especially excellent.

A compound represented by Formula (I) is a known compound, and can be obtained as described for example in F. Keller et al., LLOYDIA Vol.26, No.1, 1–15 (1963), Georg Boonen et al., Planta media Vol.64, 504–5506 (1998), JP-A-2001-316260, JP-A-8-133941 and Torsten Reffstrup et al., Acta Chemica Scandinavica B30 613–618 (1976).

While some of the compounds represented by Formula (I) have not been reported so far depending on combinations of their substituent groups, they can be synthesized in accordance with the methods described in the references mentioned above.

The active compound of the wood preservative of this invention may be its glycoside, and a sugar moiety of the glycoside may be exemplified by glucose, galactose and rhamnose.

A wood preservative, that is, a wood attacking-, decaying- and staining-inhibitory composition according to the invention may be formulated in any dosage form as long as it contains an active material mentioned above.

A wood preservative of the invention may also be present as a composition. Such a composition may for example be a liquid composition such as solutions, wettable powders, suspensions, dispersions, emulsions, oils and lotions; a solid composition such as powders, granules, microcapsules, microspheres, fluidizing compositions and foams; a semi-solid composition such as pastes and creams; sprays and aerosols; coating compositions and the like, any of which may be selected appropriately in view of the purpose of use or the site of application. Any of the compositions can be produced by a known method.

A liquid composition mentioned above can be produced for example by diluting a compound with a suitable solvent, diluent or carrier. For producing a wettable powder, a solid diluent or carrier may further be added.

A liquid diluent or carrier mentioned above may include, in addition to the extraction solvents mentioned above, a plasticizer (for example, an ester-based plasticizer such as di-2-ethylhexyladipate); a petroleum-based solvent such as kerosene; an aromatic hydrocarbon such as ethylnaphthalene and phenylxylylethane; a phosphate such as 2-ethylhexylphenylphosphate and the like. Any of these liquid diluent or carrier may be employed alone or in combination with each other. A solid diluent or carrier described above may for example be kieselguhr, mica, clay, kaolin, talc, quartz powder, bentonite and the like. Similarly, any of these solid diluent or carrier may be employed alone or in combination with each other.

A solid composition described above can be produced for example by diluting or granulating the plant or the processed product thereof or a compound described above with a suitable solid diluent or carrier. The solid diluent or carrier may for example be a solid diluent exemplified above as well as a mineral powder including a talc such as talcum powders and wax powders, a clay such as a finely powdered clay and calcium carbonate; a vegetable powder such as wood powders, activated carbons and starches; various carriers employed widely for pesticides and horticultural preparations. Any of these solid diluents and carriers is frequently employed also as an extender. Any of the solid diluents and carrier may be employed singly or in combination with each other.

An aerosol described above can be produced for example by diluting a compound described above if necessary with a suitable solvent followed by charging together with a propellant under pressure in a container. The solvent may for example be a solvent exemplified above. The propellant may be an alcohol, for example, propyl alcohol and a liquefied natural gas.

The wood preservative of wood preserving composition of the invention may also contain, depending on the type of the composition and if necessary, various additives including anti-decaying and anti-fungal agents; stabilizers such as antioxidants and UV ray absorbers; binders; film forming resins; emulsifiers, dispersants, wetting agents, moistening agents, penetrating agents; thickening agents; fluidizing promoters; anti-coagluating agents; flocculating agents; UV Ray-scattering agents; dehydrating agent; colorants and the like.

An anti-decaying and anti-fungal agent described above may for example be an organic iodine-containing compound such as 3-bromo-2,3-diiodo-2-propenylethyl carbonate, 3-iodo-2-propynylbutyl carbamate, 2,3,3-triiodoallyl alcohol and p-chlorophenyl-3-iodopropargyl formal; a benzimidazole- or benzothiazole-based compound such as 2-(4-thiazolyl)benzimidazole and 2-thiocyanomethyl thiobenzothiazole; a triazole-based compound such as 1-(2-(2',4'-dichlorophenyl)-1,3-dioxolan-2-ylmethyl)-1H-1,2,4-triavole, 1-(2-(2',4'-dichlorophenyl)-propyl-1,3-dioxolan-2-ylmethyl)-1H-1,2,4-triazole, α-(2-(4-chlorophenyl) ethyl)-α-(1,1-dimethylethyl)-1H-1,2,4-triavole-1-ethanol and α-(4-chlorophenyl)-α-(1-cyclopropylethyl)-1H-1,2,4-triazole-1-ethanol and; an organic zinc compound such as zinc bis-(2-pyridine-thiole-1-oxide) phthalate; a benzoic acid-based compound such as 4-isopropyltropolone (hinokitiol), benzoic acid, sodium benzoate and n-butyl p-oxybenzoate and a natural compound such as borax.

An antioxidant may for example be a phenolic antioxidant such as 4,4'-thiobis-6-t-butylmethylphenol, butylated hydroxyanisole (mixture of 2-t-butyl-4-methoxypgenol and 3-t-butyl-4-methoxyphenol), p-octylphenol, mono (di or tri)-(α-methylbenzyl) phenol, 2,6-di-t-butyl-p-cresol (BHT) and pentaerythrithyl tetrakis [3-(3,5-di-t-butyl-4-hydroxyphenyl)] propionate; an amine-based antioxidant such as N,N'-di-2-naphthyl-p-phenylene diamine; a hydroquinoline-based antioxidant such as 2,5-di(t-amyl) hydroquinoline; a sulfur-based antioxidant such as dilauryl thiodipropionate; a phosphorus-based antioxidant such as triphenyl phosphite and the like.

A UV ray absorbing agent may for example be a benzotriazole-based compound such as 1-(2'-hydroxy-5'-methylphenyl) benzotriazole and 2-(2'-hydroxy-4'-n-octoxyphenyl) benzotriazole; a benzophenone-based compound such as 2-hydroxy-4-methoxybenzophenobe and 2-hydroxy-4-n-octoxybenzophenone; a salicylic acid-based compound such as phenyl salicylate and p-t-butylphenyl salicylate; 2-ethylhexyl- 2-cyano-3,3-diphenyl acrylate, 2-ethoxy-2'-ethyloxalic acid bisanilide and dimethyl succinate-1-(2-hydroxyethyl)-4-hydroxy-2,2,6,6- tetramethylpiperidine poly-condensate and the like.

A film-forming resin may for example be a thermoplastic resin such as polyolefins including polyethylene and polypropylene, polyvinyl acetate, polyvinyl alcohol, acryl resins, polyvinyl chloride, styrene resins, fluorine resins, chlorinated polyolefins, alkyd resins, polyamides and polyesters; a thermosetting resin such as phenol resins, urea resins, melamine resins, furan resins, unsaturated polyester resins and epoxy resins and the like.

As an emulsifier, dispersant, wetting agent, moistening agent or penetrating agent, a conventional surfactant including anionic and nonionic surfactants can be employed. An anionic surfactant may for example be a metallic soap or a sulfate such as sodium alkyl sulfates, an alkylbenzene sulfonate such as sodium alkylbenzene sulfonates, an alkylnaphthalene sulfonate such as sodium alkylnaphthalene sulfonates, a dialkyl 2-sulfosuccinate such as sodium dialkyl 2-sulfosuccinate, a polycarboxylic acid surfactant, an α-olefin sulfonate, a polyoxyethylene distyrene-linked phenyl ether sulfate ammonium salt, sodium lignosulfonate, potassium lignosulfonate and the like. A nonionic surfactant may for example be a polyoxyethylene alkyl ether, a polyoxyethylene alkylaryl ether, a polyoxyethylene aryl ether, a fatty polyhydric alcohol ester, a fatty polyhydric alcohol ester, a fatty polyhydric alcohol polyoxyethylene, a sucrose fatty ester, a block copolymer of ethylene oxide and propylene oxide.

A thickening agent may for example be a polyvinyl alcohol, xanthan gum, Gellan gum, a polyacrylic acid and a salt thereof, while a fluidizing promoter may for example be an organic lubricant such as PAP aids (for example, isopropylphosphoric acid), waxes, polyethylenes, fatty acid metal salts, paraffins and silicone oils and an inorganic lubricant such as talc. An anti-coagluating agent may for example be a white carbon, kieselguhr, magnesium stearate, aluminium oxide and titanium dioxide. An aggregating agent may for example be liquid paraffin, ethylene glycol diethylene glycol-triethylene glycol- isobutylene copolymer, and the like. A UV Ray-scattering agent may for example be titanium dioxide. A dehydrating agent may for example be a desiccant such as anhydrous gypsum and silica gel powders. A colorant may for example be an organic or inorganic pigment or dye.

A wood preservative according to the invention may contain other insecticides or harmful insect repellents as well as potency enhancing agents. Such other insecticides may for example be organophosphates such as phoxim, chlorpyrifos, fenitrothion, pyridaphenthion and isophenphos; a carbamate such as bassa and propoxur; a pyrethroid compound such as cyfluthrin, permethrin, tralomethrin, fenvalerate, ethofenprox and silafluofen; a neonicotinoid compound such as imidacloprid, nitenpyram, acetamiprid and clothianidin, a phenylpyrazole compound such as fipronil, nereistoxin-based compound such as bensultap, etc., chlorphenapyr, a hiba oil, a hiba neutral oil, fatty acids such as decanoic acid and octanoic acid (Japanese Patent 2925081), octanol, lauryl alcohol, decanol, isodecanol, methyl caprynate, methyl caprylate (Japanese Patent 2919280) and boric acid, as well as plants such as neem (JP-A-3-41011), genus Moringa and genus Marah (JP-A-6-329514). A chitin synthesis inhibitor also known as an insect growth regulator (IGR) such as lufenuron, hexaflumuron, diflubenzuron and flufenoxuron and a juvenile hormone analogue such as methoprene and hydroprene may also be contained.

The amount of an active material described above, i.e., a plant or a processed matter from the plant, for example, an extract or an exudate, to be contained in the preparation may vary depending on the dosage form and the application mode of a wood preservative. In a liquid, semi-solid or solid composition, the concentration of a component described above in a wood preservative may for example be 0.1 to 100% by weight, preferably 0.5 to 50% by weight as a plant, an extract or exudate of herbal medicine described above. In a wood preservative as an aerosol, the concentration of a component described above in the content of a container may for example be 0.01 to 25% by weight, preferably 0.05 to 15% by weight as an extract or exudate of a plant described above.

The amount of an active ingredient the compound represented by the formula (I) described above to be contained may vary depending on the dosage form and the application mode of a wood preservative. In a liquid, semi-solid or solid composition, the concentration of a component described above in a wood preservative may for example be 0.01 to 80% by weight, preferably 0.1 to 30% by weight as the compound described above. In a wood preservative as an aerosol, the concentration of a component described above in the content of a container may for example be 0.01 to 20% by weight, preferably 0.05 to 10% by weight as the compound described above.

A wood preservative of the invention can be applied to an insect harmful to a wood, a wood rot fungus and a wood-staining fungus, especially to termites that are insects harmful to wood. The insect harmful to a wood, which is a target of a wood preservative according to the invention, may for example be any of those listed below. Examples include insects of Isoptera, Coleoptera and Hymenoptera. Examples of the Isoptera insects described above are Rhinotermitidae termites such as *Reticulitermes speratus* and *Coptotermes formosanus* and *Kalotermitidae* termites such as *Cryptotermes domesticus* and *Incisitermes minor*. Examples of the coleoptera insects described above are Cucujidae insects such as *Lyctus brunneus* stephens, *Lyctus linearis* and *Lycrus sinensis*, Anobiidae insects such as *Nicobium hirtum, Ernobius mollis, Ptilineurus marmoratus* and *Sculptotheca hilleri*, Bostrychidae insects such as *Dinoderus minutus, Dinoderus japonicus, Rhizopertha dominica* and *Heterobostrychus hamatipennis*, Cerambycidae insects such as *Stromatium longicorne*, Rhynchophoridae insects such as Rhynchophory, Scolytidae insects such as *Xyleborus saxeslni*, as well as Buprestidae insects and Curculionidae insects. Examples of the Hymenoptera insects described above are Anthophoridae insects such as *Xylocopa appendiculata* circumvolans and Formicidae insects such as *Camponotus obscuripes*. A wood-decaying fungus as a target of the wood preservative according to the invention is any of various fungi including a brown-rot fungus, for example, *Fomitopsis palustris, Coniophora puteana, Gloeophyllum saepiarium, Gloeophyllum trabeum* and *Serpula lacrymans* and a white-rot fungus, for example, *Trametes versicolor*. A wood-staining fungus as a target of a wood preservative of the invention may for example be *Aspergillus niger* and *Aureobasidium pullulans*. When a wood preservative of the invention is employed for controlling a harmful insect, especially a house insect such as termites, and also against a wood rot fungus and wood staining fungus, then a highly efficient control is possible at a low dose.

This effect can be obtained also by using a plant itself such as a stem root, leaf or fruit that contains an extract or an exudate described above.

In a method for protecting a wood using an inventive wood preservative, the wood preservative described above is applied to a site of the invasion by or the occurrence of a harmful insect or a wood decaying or staining fungus, such as corners of kitchens, bathrooms, living rooms, floors, under the floors, ceilings, house foundations, pillars, walls, wooden ware such as furniture and soils. Such a method for applying a wood preservative includes various modes, for example application, dusting, immersion, infusion, mixing and spraying, depending on the site of the invasion by or the occurrence of a wood-eating harmful insect and a wood rotting or staining microorganism. Such a treatment method is not limited particularly as long as a wood can be protected, and it is also possible to employ, in addition to a direct application to a wood, an application to a basal heat insulating material or a composition may be buried in a soil. It is also possible to mix a composition for example with an adhesive, which is then applied to plywood, a composite board or a woody board. When a composition is applied into a soil, it may be sprayed onto the surface of the soil or into a groove formed on the soil or may be mixed with the soil. A wood preservative can also be utilized effectively in such a way that it is incorporated into a sheet substrate such as synthetic resin sheets, papers or fabrics by means of application, impregnation or kneading to form a sheet composition, which is then mounted on or applied to a site of the invasion by or the occurrence of a harmful insect described above.

A wood preservative of the invention is excellent in preventing the ingestion of a wood by an insect harmful to the wood and preventing the onset and the growth of a wood-rot fungus or a wood-staining fungus while being highly safe to humans and animals without exerting no adverse effect on the environment.

EXAMPLES

The present invention is further detailed in the following Examples and Experiments, which are not intended to restrict the invention. Percent % shows weight % otherwise specified.

Example 1

100 g of the stems of *Piper methysticum* plant was extracted with 800 ml of acetone under reflux at 60° C. The extract was concentrated under reduced pressure to obtain a concentrate. The concentrate was dissolved in methanol to form a 10% solution of the concentrate in methanol.

Example 2

100 g of dried stems of *Piper methysticum* plant obtained as the extraction residue in Example 1 was extracted with 800 ml of methanol under reflux at 60° C. The extract was concentrated under reduced pressure to obtain a concentrate. The concentrate was dissolved in methanol to form a 10% solution of the concentrate in methanol.

Example 3

100 g of the leaves of *Piper methysticum* plant was extracted with 800 ml of acetone under reflux at 60° C. The extract was concentrated under reduced pressure to obtain a concentrate. The concentrate was dissolved in methanol to form a 10% solution of the concentrate in methanol.

Example 4

100 g of dried leaves of *Piper methysticum* plant obtained as the residue in Example 3 was extracted with 800 ml of methanol under reflux at 60° C. The extract was concentrated under reduced pressure to obtain a concentrate. The concentrate was dissolved in methanol to form a 10% solution of the concentrate in methanol.

Experiment 1
Anti-Fungal Activity Test

A wood piece (beech, sectional area: 20×3 mm, length: 50 mm, 6 pieces in total) was immersed in the methanol solution of the concentrate of Example 1, 2, 3 or 4 respectively, for 3 minutes and then air-dried. The wood piece was placed on a 2% agar plate in a petri dish of 90 mm in diameter and 20 mm in depth via a mesh cover which served to avoid a direct contact between the agar and the wood piece. The piece was sprayed with 2 ml of the spore mixture of Aspergillus niger, Penicillin funculosum, Aureobasidium pullulans and Gliocladium virens, and the growth conditions were observed.

Tests applying the respective anti-fungal compositions of Examples 1 to 4 gave the results after 4 weeks in Table 1.

The scores are on the basis of the criteria shown in Table 2 and numbers are average of 10 tests.

TABLE 1

| Sample | After 4 weeks |
| --- | --- |
| Methanol solution of concentrate of Example 1 | 1.1 |
| Methanol solution of concentrate of Example 2 | 1.5 |
| Methanol solution of concentrate of Example 3 | 1.3 |
| Methanol solution of concentrate of Example 4 | 1.5 |
| Control | 3.0 |

TABLE 2

| Scores | Fungal growth condition |
| --- | --- |
| 0 | No fungal growth on test piece |
| 1 | Fungal growth only on side of test piece |
| 2 | Fungal growth on not more than 1/3 of top surface of test piece |
| 3 | Fungal growth on more than 1/3 of top surface of test piece |

Experiment 2
Anti-Decaying Activity Test-1

A cedar piece (20×40×5 mm, 2-way strait-grained wood) whose cut end was sealed with an epoxy resin was coated with 100 g/m² of the methanol solution of the concentrate of Example 1 or the methanol solution of the concentrate of Example 2. It was dried at 60° C. for 2 days, and then weighed to record the weight before the test. After sterilizing with an ethylene oxide gas, the piece was placed on a petri dish containing a medium inoculated with Fomitopsis palustris or Trametes versicolor. After allowing it to stand for 12 weeks, the piece was taken out and dried at 60° C. for 2 days, and then weighed to calculate a percent weight loss.

The results are shown in Table 3.

TABLE 3

| | Percent weight loss | |
| --- | --- | --- |
| Sample | Fomitopsis palustris | Trametes versicolor |
| Methanol solution of concentrate of Example 1 | 1.7 | 1.9 |
| Methanol solution of concentrate of Example 2 | 9.2 | 4.3 |
| Control | 33.6 | 21.2 |

Anti-Decaying Activity Test-2

A cedar piece (20×40×5 mm, 2-way strait-grained wood) whose cut end was sealed with an epoxy resin was coated with 100 g/m² of the methanol solution of the concentrate of Example 3 or the methanol solution of the concentrate of Example 4. It was dried at 60° C. for 2 days, and then weighed to record the weight before the test. After sterilizing with an ethylene oxide gas, the piece was placed on a petri dish containing a medium inoculated with Fomitopsis palustris or Trametes versicolor. After allowing it to stand for 12 weeks, the piece was taken out and dried at 60° C. for 2 days, and then weighed to calculate a percent weight loss.

The results are shown in Table 4.

TABLE 4

| | Percent weight loss | |
| --- | --- | --- |
| Sample | Fomitopsis palustris | Trametes versicolor |
| Methanol solution of concentrate of Example 3 | 1.9 | 2.2 |
| Methanol solution of concentrate of Example 4 | 9.5 | 5.3 |
| Control | 34.6 | 22.2 |

Experiment 3
Anti-Termite Activity Test-1
(1) Contact Test 100 g of each sample shown in Table 5 was boiled with 800 ml of each extraction solvent shown in Table 5 under reflux to obtain an extract. The extract was concentrated under reduced pressure into dryness, whereby obtaining a concentrate. The concentrate was dissolved in the extraction solvent to obtain a 20% solution of the concentrate. A 10 g aliquot was added to a silica sand to allow the sand to carry 1% of the concentrate, and then water was added to allow the sand to contain 10% of water. The entire mass was transferred to a petri dish, to which 10 workers of Coptotermes formosanus were released for observation.

The results of the contact test performed as described above are shown in Table 5.

TABLE 5

| Sample | Extraction solvent | After 2 hours | After 4 hours | After 6 hours | After 1 day | After 4 day |
| --- | --- | --- | --- | --- | --- | --- |
| Piper methysticum stem | Acetone | 8-2-0 | 5-5-0 | 5-5-0 | 1-1-8 | 0-0-10 |
| Piper methysticum stem | Methanol | 10-0-0 | 10-0-0 | 8-2-0 | 8-0-2 | 5-0-5 |
| Piper methysticum leaf | Acetone | 8-2-0 | 6-4-0 | 6-4-0 | 1-3-6 | 0-0-10 |
| Piper methysticum leaf | Methanol | 10-0-0 | 10-0-0 | 8-2-0 | 8-1-1 | 5-2-3 |
| Control | — | 10-0-0 | 10-0-0 | 10-0-0 | 10-0-0 | 10-0-0 |

Scores in Table: Number of termites showing respective conditions:

Normal-Knockdown-Death (2) Attacking Inhibition Test

Similarly to Experiment 3, a sample shown in Table 6 was extracted with the respective solvent shown in Table 6 to obtain a sample concentrate.

This sample concentrate was dissolved in the extraction solvent to form a 10% solution, with which a No.2 filter paper of 1 cm×1 cm in size was impregnated shortly prior to drying at room temperature. This filter paper sample was placed in a population of the workers of Coptotermes formosanus (100 workers per sample), which were observed for the attacking (ingestion) inhibition.

The attacking inhibition test performed as described above gave the results shown in Table 6.

TABLE 6

| Sample | Extraction solvent | Observation results |
|---|---|---|
| *Piper methysticum* stem | Acetone | No attacking |
| *Piper methysticum* leaf | Acetone | No attacking |
| Non-treated | | Attacked completely by ingestion |

(3) Boring Test-1

Figure 1:
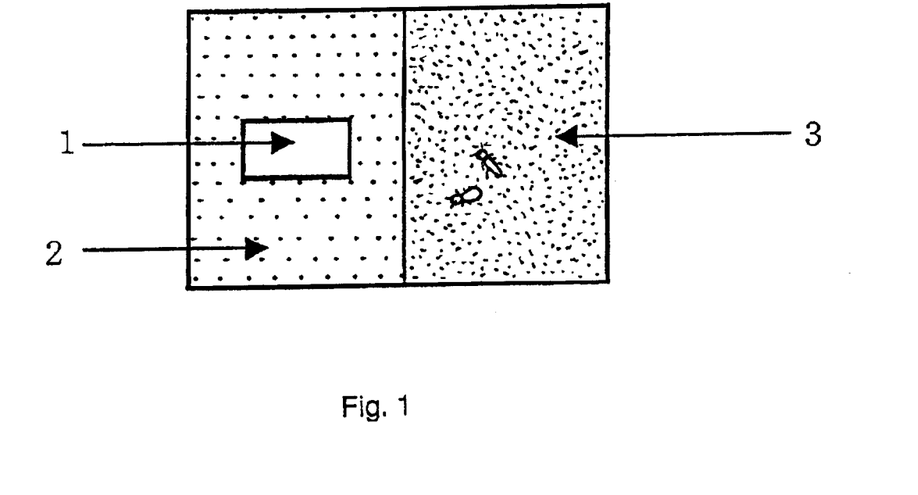
FIG. 1: A top view of an apparatus for the boring test.
Figure 2:
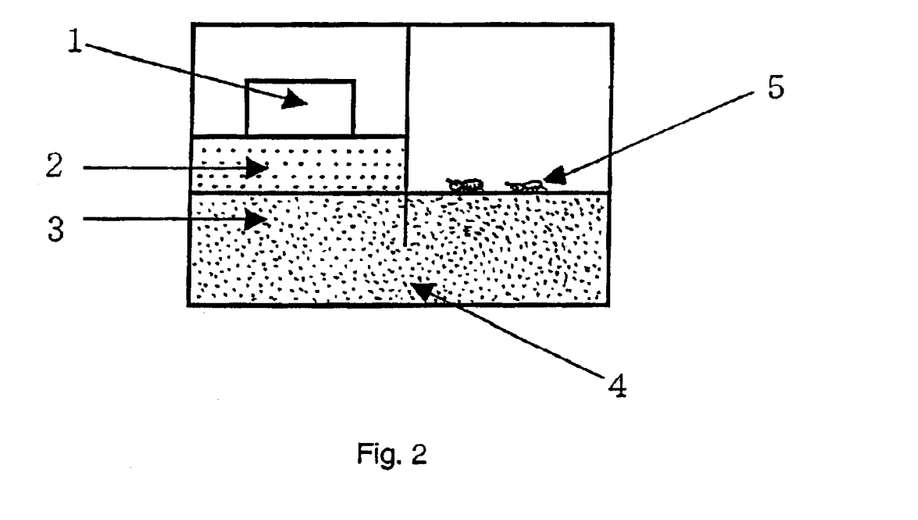
FIG. 2: A side view of an apparatus for the boring test.

As shown in FIG. 1, a soil was filled to a depth of about 1 cm in a container having a gateway or passage of about 0.3 cm in height and 4 cm of width below the connection site of connected cubes each of 50 cm in length, 50 cm in width and 50 cm in height. One cube was filled with a pulverized stems of *Piper methysticum* plant to a depth of about 1 cm, on which a pine bait of 2 cm in length having the cut end of 1 cm×1 cm was placed. Thereafter, 200 workers of Coptotermes formosanus were released to the non-treatment soil and observed for 3 weeks to examine for the ability of boring the pulverized *Piper methysticum* stems to reach the bait.

Results:

The pulverized *Piper methysticum* stems were not bored. All insects were died after 2 weeks.

In the non-treatment group, the insects reached the bait after 1 day, and were healthy even after 3 weeks.

(3) Boring test-2

As shown in FIG. 1, a soil was filled to a depth of about 1 cm in a container having a gateway or passage of about 0.3 cm in height and 4 cm of width below the connection site of connected cubes each of 50 cm in length, 50 cm in width and 50 cm in height. One cube was filled with a pulverized leaves of *Piper methysticum* to a depth of about 1 cm, on which a pine bait of 2 cm in length having the cut end of 1 cm×1 cm was placed. Thereafter, 200 worker ants of *Coptotermes formosanus* were released to the non-treatment soil and observed for 3 weeks to examine for the ability of boring the pulverized *Piper methysticum* leaves to reach the bait.

Results:

The pulverized *Piper methysticum* leaves were not bored. All termites were died after 2 weeks.

In the non-treatment group, the termites reached the bait after 1 day, and were healthy even after 3 weeks.

Example 5

Soil Treatment Composition

A composition containing the following components was prepared.

| | |
|---|---|
| *Chamaecyparis obtusa* powder (2 mm) | 50% |
| 7,8-Dihydrokawain | 30% |
| Dispersant (Emulgen 2025G by Kao) | 10% |
| Carnauba wax | 10% |
| | 100% |

Example 6

Soil Treatment Composition

| | |
|---|---|
| *Chamaecyparis obtusa* powder (2 mm) | 40% |
| 7,8-Dihydrokawain | 10% |
| Capric acid | 40% |
| Dispersant (Emulgen 2025G by Kao) | 10% |
| | 100% |

Example 7

Soil Treatment Composition

| | |
|---|---|
| *Chamaecyparis obtusa* powder (2 mm) | 10% |
| *Thuja occidentalis* powder (2 mm) | 10% |
| 7,8-Dihydrokawain | 10% |
| *Curcuma longa* (80 mesh) | 10% |
| *Sophora subprosarata* (40 mesh) | 10% |
| *Atractylodes chnensis* (40 mesh) | 10% |
| *Piper methysticum* (40 mesh) | 30% |
| Dispersant (Emulgen 2025G by Kao) | 10% |
| | 100% |

In Examples 5 to 7 described above, 7,8-dihydrokawain was prepared as an acetone solution, which was subjected repeatedly to mixing with the *Chamaecyparis obtusa* powder followed by drying, whereby achieving desired concentrations. Each composition of Examples 5 to 7 can be dusted as a wettable powder after a 5- to 10-folud dilution with water, or it may be filled in a lesion of a wood directly as a powder or after diluting with water.

Example 8

Wood Treatment Oil

| | |
|---|---|
| 7,8-Dihydrokawain | 10% |
| Propylene glycol | 70% |
| Solvent (Isofol 14T by Condea) | 29% |
| | 100% |

Example 9

Wood Treatment Oil

| | |
|---|---|
| Kawain | 0.5% |
| 7,8-Dihydrokawain | 1.0% |
| Methysticin | 0.5% |
| Propylene glycol | 80.0% |
| Solvent (Isofol 14T by Condea) | 18.0% |
| | 100.0% |

Example 10

Wood Treatment Oil

| | |
|---|---|
| Kawain | 0.5% |
| 7,8-Dihydrokawain | 10% |
| Methysticin | 0.5% |
| Propylene glycol | 80.0% |
| Solvent (Isofol 14T by Condea) | 17.0% |
| IPBC | 1.0% |
| | 100.0% |

Example 11

Wood Treatment Emulsion

| | |
|---|---|
| 7,8-Dihydrokawain | 1.0% |
| Propylene glycol | 30.0% |
| Solvent (Isofol 12T by Condea) | 10.0% |
| Dispersant (Emulgen 2025G by Kao) | 7.0% |
| Water | 52.0% |
| | 100.0% |

Example 12

Coating Composition

| | |
|---|---|
| Kawain | 0.500% |
| 7,8-Dihydrokawain | 1.000% |
| Ethanol | 64.195% |
| Linseed oil | 30.000% |
| Iron oxide | 3.000% |
| Lecithin | 0.300% |
| Talk | 1.000% |
| Cobalt octate | 0.005% |
| Total | 100.000% |

Experiment 4

Damage (Ingestion) Inhibition Test

A 1 w/w % solution of each compound shown in Table 7 in acetone (except for hispidin which was prepared as a 1 w/w % solution in methanol) was prepared.

In this solution, a No.2 filter paper of 1×1 cm in size was immersed, taken out and then air-dried. It was then placed in a 11-K bottle in which 100 worker ants of *Coptotermes formosanus* had been kept, and the ingestion behavior was observed. Hispidin employed was a reagent produced by Calbiochem. The results are shown in Table 7.

TABLE 7

| | Damage degree after 1 week |
|---|---|
| Kawain | 1 |
| 7,8-Dihydrokawain | 0 |
| 5,6-Dehydrokawain | 1 |
| Yangonin | 1 |
| Methysticin | 0 |
| 5,6,7,8-Tetrahydroyangonin | 0 |
| 7,8-Dihydromethysticin | 0 |

TABLE 7-continued

| | Damage degree after 1 week |
|---|---|
| Hispidin | 1 |
| Control | 4 |

Scores in Table (degree of damage)
0: No damage
1: Damage of ½ or less
2: Damage of ½ to ¾
3: Damage of ¾ with some remainder
4: Complete damage Experiment 5

(1) Wood-Decaying Fungal Growth Inhibition Test

A 5 w/w % acetone solution of each compound shown in Table 8 was prepared.

A No.2 filter paper of 1×1 cm in size was immersed in the solution, taken out and then air-dried. The filter was then placed on a *Fomitopsis palustris* which had been cultivated on a PDA medium in a petri dish and observed conditions of fungal growth for 8 weeks. The results were summarized in Table 8.

TABLE 8

| | Fungal growth after 8 weeks |
|---|---|
| Kawain | 0 |
| 7,8-Dihydrokawain | 0 |
| 5,6-Dehydrokawain | 0 |
| Yangonin | 0 |
| Methysticin | 0 |
| 5,6,7,8-Tetrahydroyangonin | 0 |
| 7,8-Dihydromethysticin | 0 |
| Control | 1 |

Scores in Table (degree of growth)
0: No growth
1: Fungal growth

Experiment 6

Woodstaining Fungal Growth Inhibition Test

A 5 w/w % acetone solution of each compound shown in Table 9 was prepared. In the solution, a No.2 filter paper of 1×1 cm in size was immersed, taken out and then air-dried. To the resultant filter paper, about 2 ml of the suspension of a spore mixture of the 4 wood-staining microorganism was sprayed, and the growth of the fungi on a 2% agar medium in a petri dish was observed for 3 days. The results are shown in Table 9.

Staining Fungi Employed:

*Aspergillus niger*

*Penicillin funculosum*

*Aureobasidium pullulans* and

*Gliocladium virens*

TABLE 9

| | Fungal growth after 3 days |
|---|---|
| Kawain | 0 |
| 7,8-Dihydrokawain | 0 |
| 5,6-Dehydrokawain | 0 |
| Yangonin | 0 |
| Methysticin | 0 |
| 5,6,7,8-Tetrahydroyangonin | 0 |

TABLE 9-continued

| | Fungal growth after 3 days |
|---|---|
| 7,8-Dihydromethysticin | 0 |
| Control | 1 |

Scores in Table (degree of damage)
0: No fungal growth
1: Fungal growth

What is claimed is:

1. A method for preserving wood which comprises treating wood with an effective amount of a *Piper methysticum* plant or processed product thereof, or a compound represented by Formula (I).

wherein $R^1$, $R^2$, $R^3$, $R^4$ and $R^{16}$ are same or different and each denotes a hydrogen atom, hydroxy or a $C_{1-4}$ alkoxy, or $R^1$ and $R^2$ are taken together to form a group represented by —O—$(CH_2)_n$—O— wherein n is an integer of 1 to 3, $R^5$ is a $C_{1-4}$ alkoxy and X is —CH=CH—, —$CH_2$—$CH_2$— or epoxyethylene, and the bond:

denotes a single bond or a double bond.

2. The method according to claim 1 wherein preserving wood is controlling an insect harmful to wood.

3. The method according to claim 1 wherein preserving wood is preserving rotting of wood.

4. The method according to claim 1 wherein preserving wood is exterminating fungus.

5. The method according to claim 1 wherein preserving wood is controlling a termite.

6. The method according to claim 1 wherein *Piper methysticum*. plant or processed product thereof is a stem, leaf or root of the plant.

7. The method according to claim 6 wherein the processed products thereof is a dry powder or an extract of a *Piper methysticum* stem, leaf or root.

8. The method according to claim 1 wherein the compound represented by the formula (I) is a compound represented by Formula (II):

wherein $R^6$ is hydroxy or a $C_{1-4}$ alkoxy, $R^7$ is a hydrogen atom, hydroxy or a $C_{1-4}$ alkoxy, or $R^6$ and $R^7$ are taken together to form a group represented by O—$(CH_2)_n$—O— wherein n is 1 or 2, $R^8$ is a hydrogen atom or a $C_{1-4}$ alkoxy, $R^9$ is hydroxy or a $C_{1-4}$ alkoxy, $R^{17}$ is a hydrogen atom, hydroxy or a $C_{1-4}$ alkoxy and X is defined as described above, or a compound represented by Formula (III):

wherein $R^{10}$ is a hydrogen atom, hydroxy or a $C_{1-4}$ alkoxy, $R_{11}$ is a hydrogen atom or hydroxy, or $R^{10}$ and $R^{11}$ are taken together to form a group represented by —O—$(CH_2)_n$—O— wherein n is 1 or 2, $R^{12}$ is a hydrogen atom or hydroxy, $R^{13}$ is a $C_{1-4}$ alkoxy and $R^{18}$ is a hydrogen atom, hydroxy or a $C_{1-4}$ alkoxy X is defined as described above.

9. The method according to claim 1 wherein a compound represented by Formula (I) is:

(1) kawain, or kavain
(2) 7,8-dihydrokawain,
(3) yangonin,
(4) 5,6,7,8-tetrahydroyangonin,
(5) methysticin,
(6) 7,8-dihydromethysticin,
(7) cis-5-hydroxykawain,
(8) 11-methoxy-12-hydroxy-5,6-dehydrokawain,
(9) 7,8-dihydroyangonin,
(10) 5,6-dihydroyangonin,
(11) 11-methoxyyanogonin,
(12) 10-methoxyyangoin,
(13) 11-hydroxyyangonin or,
(14) 5,6-dehydromethysticin.

10. The method according to claim 1 wherein the compound represented by the formula (I) is a compound represented by Formula (IV):

wherein each of $R^{14}$ and $R^{15}$ is a hydrogen atom or they are taken together to form methylenedioxy, and X is defined as described above.

* * * * *